United States Patent [19]

Goldstein

[11] 4,011,870
[45] Mar. 15, 1977

[54] NEEDLE INSTRUMENT

[76] Inventor: Michael Goldstein, 192 15C 67th Ave., New York, N.Y. 11635

[22] Filed: Mar. 5, 1976

[21] Appl. No.: 664,327

[52] U.S. Cl. ............................... 128/276; 128/340; 128/218 N; 128/305

[51] Int. Cl.$^2$ ......................................... A61B 17/32

[58] Field of Search ...... 128/276, 278, 329, 218 N, 128/305 R, 339, 340, 321

[56] References Cited

UNITED STATES PATENTS

| | | | |
|---|---|---|---|
| 919,138 | 4/1909 | Drake et al. | 128/340 |
| 1,377,359 | 5/1921 | Littlejohn | 128/339 |
| 3,452,755 | 7/1969 | Mishkin et al. | 128/340 |
| 3,807,406 | 4/1974 | Rafferty et al. | 128/318 |
| 3,828,781 | 8/1974 | Rothman | 128/278 |
| 3,882,849 | 5/1975 | Jamshidi | 128/329 |
| 3,902,495 | 9/1975 | Weiss et al. | 128/276 |

*Primary Examiner*—Robert W. Michell
*Assistant Examiner*—Henry J. Recla
*Attorney, Agent, or Firm*—Frank J. Jordan

[57] ABSTRACT

A needle instrument for performing peripheral iridectomy for narrow angle glaucoma includes a hollow needle having a first right angle bend and a second U-shaped bend. An adaptor and conduit are provided for connecting the needle to a source of suction such that suction may be drawn through the open end of the needle. The needle is adapted to be grasped by a hemostat or the like along the U-shaped bend to facilitate manual manipulation during performance of a peripheral iridectomy.

6 Claims, 6 Drawing Figures

NEEDLE INSTRUMENT

BACKGROUND OF THE INVENTION

This invention relates to a needle instrument for performing a peripheral iridectomy for narrow angle glaucoma.

The needle instrument of the present invention makes it possible to perform a peripheral iridectomy for narrow angled glaucoma while making a minimum size small hole in the cornea and without having to pull out the iris through an opening in the cornea as was done heretofore. In this regard, in prior art arrangements, an opening was cut into the cornea and a tweezer or the like was used to pull out a bulging portion of the iris through the opening in the cornea and then, when this bulging portion was exposed on the outside of the cornea, a hole was cut in the iris. According to the present invention, it is not necessary to make a large hole in the cornea through which to pull the iris through nor is it necessary to pull the bulging iris through an opening in the cornea was done heretofore.

Accordingly, an object of the present invention is to provide a needle instrument for performing a peripheral iridectomy which overcomes the disadvantages of prior art arrangements.

Other features which are considered characteristic of the invention are set forth in the appended claims.

Although the invention is illustrated and described in relationship to specific embodiments, it is nevertheless not intended to be limited to the details shown, since various modifications and structural changes may be made therein without departing from the spirit of the invention and within the scope and range of equivalents of the claims.

The construction and operation of the invention, however, together with additional objects and advantages thereof will be best understood from the following description of specific embodiments when read in connection with the accompanying drawings.

SUMMARY OF THE INVENTION

A needle instrument for performing a peripheral iridectomy for narrow angle glaucoma comprises a hollow needle having a first bend and a second bend. The first bend is substantially a right angle bend and contained substantially within a single plane, while the second bend is subtantially a U-shaped bend and is disposed in a plane substantially perpendicular to the first plane. Means are provided for connecting the needle to a source of suction such that suction may be drawn through the open end of the needle. The needle instrument is adapted to be grasped by a hemostat or the like along the U-shaped bend to facilitate manual manipulation during performance of the peripheral iridectomy.

DESCRIPTION OF THE PREFERRED EMBODIMENT

Figure 1:
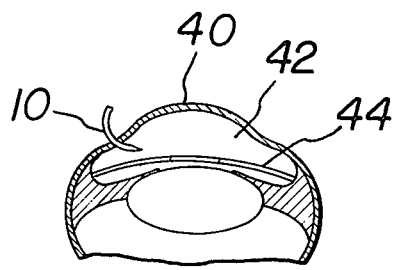
FIG. 1 is a schematic view representing a cross section of an eye and a portion of the needle instrument of the present invention according to one embodiment thereof.

The needle instrument of the present invention comprises a curved hollow needle 10 having a through passage 11 therein. The needle is connected to a conventional syringe 12 by a plastic tube 14 or the like. A connector 16 may be provided between the end of the needle and the plastic tube 14. The syringe 12 includes a manually operable plunger 18 which may be withdrawn to thereby provide a negative pressure on the outlet 20 of the needle. The plastic tube 14 along with its connections to the syringe 12 and to the connector 16 along with the connection of the connector 16 to the needle 10 are all airtight.

Figure 2:
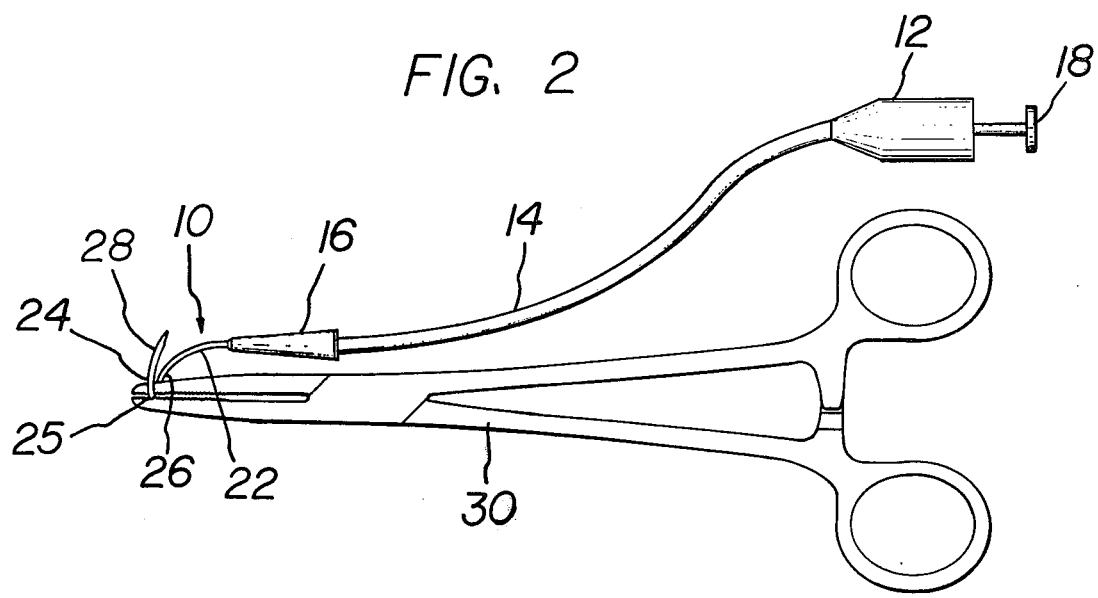
FIG. 2 is an elevational view of the needle instrument being held by a hemostat.

The needle is bent generally in two planes including a first bend 22 generally in the plane of the paper as shown in FIG. 2 and a second bend 24 in a plane which is generally perpendicular to the plane of the paper as shown in FIG. 2. The first bend 22 in the general plane of the paper (FIG. 2) is generally a right angle bend whereas the second bend 24 in the plane perpendicularly to the paper (FIG. 2) is of generally U-shaped configuration having a bottom U-shaped portion 25 and two legs 26 and 28.

As can be seen in FIG. 2, a conventional hemostat 30 is adapted to grasp the needle 10 at the U-shaped portion and thereby the needle 10 may be manipulated and controlled by manually handling the hemostat 30 as will be described hereinafter.

Figure 3:
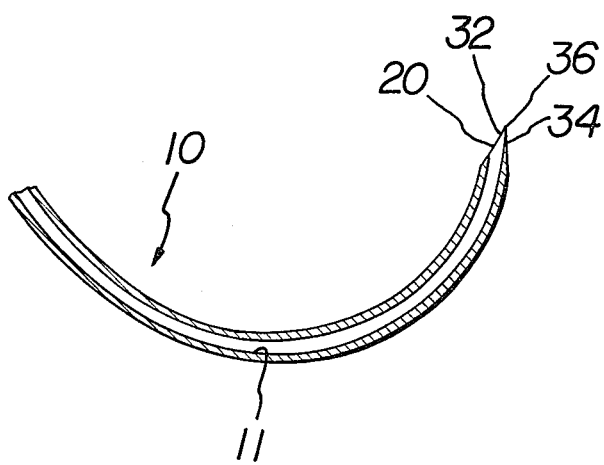
FIG. 3 is an enlarged cross sectional view of the end portion of the needle instrument.

The needle 10 has a terminating end 32 which is cut off in a plane forming an acute angle as shown in FIG. 3. In addition, the outer wall of the needle may be removed as indicated at 34 to provide a knife edge 36 as shown in FIG. 31. This knife edge 36 is utilized to effect a cutting or penetrating action as will be hereinafter described.

Figure 4:
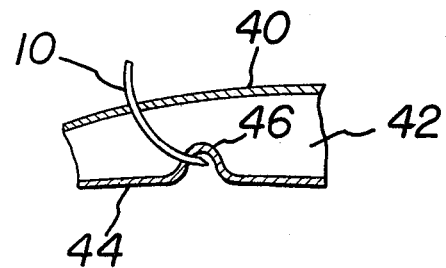
FIG. 4 is a schematic representation showing the use of the needle instrument at one stage of the operation.
Figure 5:
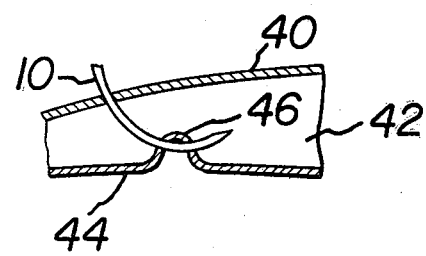
FIG. 5 is a view similar to FIG. 4 showing a further advanced stage of the operation.

The above described needle instrument 10 is utilized to perform a peripheral iridectomy for narrow angle glaucoma. As shown in FIG. 1, the needle is first passed through the cornea 40 of the eye into the anterior chamber 42. As shown in FIG. 4, the iris 44 tends to bulge outwardly as indicated at 46 into the anterior chamber 42 as a result of the fluid pressure on the iris and the reduced pressure caused by the suction provided in the needle instrument 10 through the end opening 20 of the needle and through the operation of the syringe 12 as previously described. As the iris bulges as indicated at 46, the needle instrument 10 is further manually manipulated by the hemostat 30 and inserted through the bulge 46 in the iris 44 as shown in FIG. 5 to thereby make an opening in the iris 44.

After the needle instrument 10 makes a hole in the iris 44, the needle instrument 10 is withdrawn and the hole in the iris thereby relieves the pressure therein.

The aforementioned needle instrument 10 makes it possible to perform a peripheral iridectomy for narrow angled glaucoma while making a minimum size small hole in the cornea and without having to pull out the iris through an opening in the cornea as was done heretofore. In this regard, it is noted that in prior art arrangements, an opening was cut into the cornea and a tweezer or the like was used to pull out a bulging portion of the iris through the opening in the cornea and then, when this bulging portion was exposed on the outside of the cornea, a hole was cut in the iris. According to the present invention, it is not necessary to make a large hole in the cornea through which to pull the iris through nor is it necessary to pull the bulging iris through an opening as was done heretofore.

The needle instrument 10 has a sharp end in the form of a cutting knife which enables it to perform the cutting operation in the cornea and in the iris. Moreover, the suction provided in the needle instrument 10 facilitates exposure and bulging of the iris so that the hole may be made therein as shown in FIG. 5. In addition, the curvature of the needle instrument wherein it is provided with the two bends as described above enables it to be manually operated by a hemostat which is clamped to the U-shaped bent portion of the needle instrument so that it may be manually manipulated to perform the above operation. In other words, the surgeon does not necessarily have to touch and grasp the small needle instrument but can control and manipulate the later through the hemostat which is clamped thereon.

Alternatively, the syringe may be replaced by a suitable suction device or other type of aspirating device having a manually controllable control means such as a valve or the like to control the suction drawn on the needle instrument.

Figure 6:
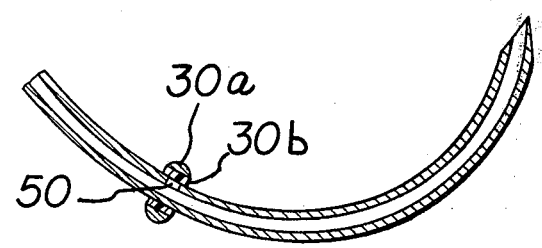
FIG. 6 is a cross sectional view, on a larger scale, similar to FIG. 3 but showing an alternate embodiment.

As a further alternative embodiment, an opening 50 may be provided in the needle instrument as shown in FIG. 6. This opening 50 may be covered or partially covered by the jaws 30a of the hemostat as shown in FIG. 6. In this way, the surgeon can control the extent that the opening 50 is exposed. This opening 50 is exposed to atmosphere and thereby controls the amount of suction at the terminating end of the needle and also permits fluid to be drawn out through the needle to provide irrigation. As indicated above, the surgeon may shift the position of the hemostat relative to the hole 50 to control the flow through such opening.

With regard to the later embodiment, a resilient material 30b such as rubber or the like may be provided on the hemostat jaws to provide a sealing and cushioning grip of the hemostat on the needle instrument and to cover the hole 50.

It is thought that the invention and many of its attendant advantages will be understood from the foregoing description and that it will be apparent that various changes may be made in the form, construction, and arrangements of the parts without departing from the spirit and scope of the invention or sacrificing all of its material advantages. The form heretofore described being merely a preferred embodiment thereof.

What is claimed is:

1. A needle instrument for performing peripheral iridectomy for narrow angle glaucoma comprising a hollow needle having a bore extending therethrough and having a first bend and a second bend, said first bend being substantially a right angle bend and contained substantially within a single plane, said second bend being substantially a U-shaped bend and being disposed in a plane subtantially perpendicular to said first plane, a source of suction and means connecting said needle to said source of suction such that suction may be drawn through said bore of said needle, said needle instrument being adapted to be grasped by a hemostat or the like along said U-shaped bend to facilitate manual manipulation during performance of the peripheral iridectomy.

2. A needle instrument according to claim 1 wherein the terminating end of said needle is an acute angle relative to the general axis of the needle.

3. A needle instrument according to claim 1 wherein the terminating end of said needle is bevelled to provide a cutting edge thereon.

4. A needle instrument according to claim 1 wherein said suction means includes a syringe, and flexible tubing connecting said syringe to said needle.

5. A needle instrument according to claim 1 including a lateral opening in said needle, said lateral opening being adapted to be covered by the jaws of a hemostat or the like during the peripheral iridectomy operation in order to control the flow through said opening.

6. A needle instrument according to claim 1 wherein said lateral opening is located in the U-shaped bend of said needle instrument.

* * * * *